United States Patent
Wong

(10) Patent No.: US 9,498,316 B1
(45) Date of Patent: *Nov. 22, 2016

(54) BIOCOMPATIBLE EXTREMELY FINE TANTALUM FILAMENT SCAFFOLDING FOR BONE AND SOFT TISSUE PROSTHESIS

(71) Applicant: COMPOSITE MATERIALS TECHNOLOGY, INC., Shewsbury, MA (US)

(72) Inventor: James Wong, Shrewsbury, MA (US)

(73) Assignee: COMPOSITE MATERIALS TECHNOLOGY, INC., Shrewsbury, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/857,614

(22) Filed: Sep. 17, 2015

Related U.S. Application Data

(63) Continuation-in-part of application No. 14/328,567, filed on Jul. 10, 2014, now Pat. No. 9,155,605.

(51) Int. Cl.
  *A61F 2/00* (2006.01)

(52) U.S. Cl.
  CPC ........... *A61F 2/0063* (2013.01); *A61F 2/0077* (2013.01); *A61F 2002/0068* (2013.01); *A61F 2002/0081* (2013.01); *A61F 2002/0086* (2013.01)

(58) Field of Classification Search
  CPC ..... A61L 27/60; A61L 27/047; A61L 27/06; A61L 27/56; A61L 2430/00; A61L 2430/02; A61L 2430/06; A61L 2430/04; A61L 2430/10; A61L 2430/32; A61L 2430/34; A61F 2/08

USPC ....................................................... 623/23.72
See application file for complete search history.

(56) References Cited

U.S. PATENT DOCUMENTS

| | | | |
|---|---|---|---|
| 3,557,795 A | 1/1971 | Hirsch | 128/335.5 |
| 3,677,795 A | 7/1972 | Bokros et al. | 117/46 |
| 4,149,277 A | 4/1979 | Bokros | 3/1 |
| 4,534,366 A | 8/1985 | Soukup | 607/121 |
| 4,846,834 A | 7/1989 | von Recum et al. | 623/11 |
| 4,945,342 A | 7/1990 | Steinemann | 174/113 |
| 4,983,184 A * | 1/1991 | Steinemann | A61F 2/08 428/546 |
| 5,030,233 A | 7/1991 | Ducheyne | 623/16 |
| 5,143,089 A | 9/1992 | Alt | 600/374 |
| 5,231,996 A | 8/1993 | Bardy et al. | 607/126 |
| 5,282,861 A | 2/1994 | Kaplan | 623/16 |
| 5,324,328 A | 6/1994 | Li et al. | 607/129 |

(Continued)

FOREIGN PATENT DOCUMENTS

| | | | | |
|---|---|---|---|---|
| WO | WO9828129 | 7/1998 | | B32B 15/00 |
| WO | WO2008039707 | 4/2008 | | H01G 9/00 |

(Continued)

OTHER PUBLICATIONS

U.S. Appl. No. 14/517,312, filed Oct. 17, 2014, Wong.

(Continued)

*Primary Examiner* — Dianne Dornbusch
(74) *Attorney, Agent, or Firm* — Hayes Soloway P.C.

(57) ABSTRACT

A tissue implant member for implanting in living tissue is provided. The implant is formed of an open structured tantalum filament having a cross-sectional size of less than about 250 microns.

16 Claims, 3 Drawing Sheets

(56) References Cited

U.S. PATENT DOCUMENTS

| | | |
|---|---|---|
| 5,869,196 A | 2/1999 | Wong et al. ............... 428/613 |
| 6,648,903 B1 | 11/2003 | Pierson ..................... 602/232 |
| 6,728,579 B1 | 4/2004 | Lindgren et al. ........... 607/116 |
| 6,780,180 B1 | 8/2004 | Goble ......................... 606/41 |
| 6,792,316 B2 | 9/2004 | Sass ........................... 607/116 |
| 6,980,865 B1 | 12/2005 | Wang et al. ............... 607/121 |
| 7,020,947 B2 | 4/2006 | Bradley ...................... 29/515 |
| 7,146,709 B2 | 12/2006 | Wong ......................... 29/599 |
| 7,158,837 B2 | 1/2007 | Osypka et al. ............. 607/122 |
| 7,235,096 B1* | 6/2007 | Van Tassel ........ A61B 5/0031 |
| | | 623/1.15 |
| 7,280,875 B1 | 10/2007 | Chitre et al. ............... 607/122 |
| 7,480,978 B1 | 1/2009 | Wong ......................... 29/599 |
| 7,490,396 B2 | 2/2009 | Bradley ...................... 29/515 |
| 7,501,579 B2 | 3/2009 | Michael et al. ........... 174/126.1 |
| 8,224,457 B2 | 7/2012 | Strandberg et al. ........ 607/116 |
| 8,460,286 B2 | 6/2013 | Stangenes .................. 606/41 |
| 2004/0121290 A1 | 6/2004 | Minevski et al. .......... 433/201.1 |
| 2005/0159739 A1 | 7/2005 | Paul ........................... 606/41 |
| 2006/0195188 A1* | 8/2006 | O'Driscoll ......... A61F 2/30756 |
| | | 623/14.12 |
| 2007/0093834 A1 | 4/2007 | Stevens et al. ............. 606/69 |
| 2007/0167815 A1 | 7/2007 | Jacobsen .................... 600/459 |
| 2007/0214857 A1 | 9/2007 | Wong et al. ............... 72/275 |
| 2007/0244548 A1 | 10/2007 | Myers et al. ............... 623/1.42 |
| 2008/0234752 A1 | 9/2008 | Dahners ..................... 606/291 |
| 2009/0018643 A1 | 1/2009 | Hashi et al. ................ 623/1.15 |
| 2009/0044398 A1 | 2/2009 | Wong ......................... 29/599 |
| 2009/0075863 A1* | 3/2009 | O'Driscoll ............ A61K 35/32 |
| | | 514/1.1 |
| 2009/0095130 A1 | 4/2009 | Smokovich et al. ........ 75/356 |
| 2009/0187258 A1 | 7/2009 | Ip et al. ...................... 623/23.72 |
| 2009/0228021 A1 | 9/2009 | Leung ........................ 606/139 |
| 2009/0234384 A1 | 9/2009 | Hadba ........................ 606/215 |
| 2010/0044076 A1 | 2/2010 | Chastain et al. ........... 174/126.2 |
| 2010/0075168 A1 | 3/2010 | Schaffer ..................... 428/544 |
| 2010/0211147 A1 | 8/2010 | Schiefer et al. ............ 607/116 |
| 2010/0280584 A1 | 11/2010 | Johnson et al. ............ 607/116 |
| 2011/0082564 A1* | 4/2011 | Liu ........................... A61F 2/28 |
| | | 623/23.72 |
| 2011/0137419 A1* | 6/2011 | Wong ....................... A61L 17/04 |
| | | 623/16.11 |
| 2012/0239162 A1* | 9/2012 | Liu ......................... A61L 27/56 |
| | | 623/23.74 |
| 2013/0282088 A1 | 10/2013 | Bondhus .................... 607/116 |

FOREIGN PATENT DOCUMENTS

| | | | | |
|---|---|---|---|---|
| WO | WO 2008/063526 | | 5/2008 | ............... B22F 1/00 |
| WO | WO2009082631 | | 7/2009 | ............... H01G 9/00 |

OTHER PUBLICATIONS

U.S. Appl. No. 14/707,944, May 8, 2015, Wong.
Office Action issued in U.S. Appl. No. 14/517,312, dated Oct. 8, 2015 (8 pgs).
U.S. Appl. No. 14/328,567, filed Jul. 10, 2014, Wong.
U.S. Appl. No. 14/494,940, Sep. 24, 2014, Wong.
U.S. Appl. No. 14/517,312, Oct. 17, 2014, Wong.
U.S. Appl. No. 14/696,130, Apr. 24, 2015, Wong.
Bobyn et al., "Characteristics of bone ingrowth and interface mechanics of a new porous tantalum biomaterials," The Journal of Bone & Joint Surgey (Br), Vo. 81-B, No. 5, Sep. 1999 (8 pgs).
Extended European Search Report issued in related application No. 10835252.7, dated May 12, 2014 (7 pgs).
Grifantini, K., "Nervy Repair Job," Technology Review, Jan./Feb. 2010, pp. 80-82 (3 pgs).
International Preliminary Report on Patentability issued in application No. PCT/US2013/060702, dated Apr. 2, 2015 (8 pgs).
International Preliminary Report on Patentability issued in application No. PCT/US2013/063915, dated Apr. 23, 2015 (7 pgs).
International Preliminary Report on Patentability issued in PCT/US2010/059124 dated Jun. 14, 2012 (6 pgs).
International Search Report and Written Opinion issued in application PCT/US14/61385, dated Mar. 17, 2015 (11 pgs).
International Search Report and Written Opinion issued in PCT/US2010/059124, dated Feb. 15, 2011 (9 pgs).
Journal article by Yarlagadda et al. entitled "Recent Advances and Current Developments in Tissue Scaffolding" published in Bio-Medical Materials and Engineering 2005 15(3), pp. 159-177 (26 pgs).
Li et al., "Ti6Ta4Sn Alloy and Subsequent Scaffolding for Bone Tissue Engineering," Tissue Engineering: Part A, vol. 15, No. 10, 2009, pp. 3151-3159 (9 pgs).
Lu, N., "Soft, flexible electronics bond to skin and even organs for better health monitoring," Technology Review, Sep./Oct. 2012 (4 pgs).
Markaki et al., "Magneto-mechanical stimulation of bone growth in a bonded array of ferromagnetic fibres," Biornaterials 25, 2004, pp. 4805-4815 (11 pgs).
Meier et al., "Cardiologist Issues Alert on St. Jude Heart Device," The New York Times, Business Day section, Aug. 22, 2012, pp. B1-B2, (2 pgs).
Office Action issued in related U.S. Appl. No. 12/961,209, dated Jul. 5, 2012 (12 pgs).
Office Action issued in related U.S. Appl. No. 13/713,885, dated May 10, 2013 (12 pgs).
Office Action issued in related U.S. Appl. No. 13/713,885, dated Aug. 8, 2013 (7 pgs).
Office Action issued in related U.S. Appl. No. 13/713,885, dated Oct. 30, 2013 (11 pgs).
Office Action issued in related U.S. Appl. No. 14/030,840, dated Jul. 17, 2014 (13 pgs).
Office Action issued in related U.S. Appl. No. 14/030,840, dated Apr. 9, 2014 (13 pgs).
Office Action issued in related U.S. Appl. No. 14/030,840, dated Dec. 13, 2013 (9 pgs).
Office Action issued in related U.S. Appl. No. 14/174,628, dated Jun. 10, 2014 (19 pgs).
Office Action issued in related U.S. Appl. No. 14/328,567, dated Feb. 25, 2015 (24 pgs).
Office Action issued in related U.S. Appl. No. 14/328,567, dated Apr. 1, 2015 (11 pgs).
Office Action issued in related U.S. Appl. No. 14/328,567, dated May 28, 2015 (19 pgs).
Office Action issued in related U.S. Appl. No. 14/494,940, dated Nov. 18, 2014 (14 pgs).
Office Action issued in related U.S. Appl. No. 14/517,312, dated Jun. 23, 2015 (40 pgs).
Office Action issued in related U.S. Appl. No. 14/517,312, dated May 29, 2015 (6 pgs).
PCT. International Search Report and Written Opinion issued in corresponding application No. PCT/US13/60702, dated Dec. 5, 2013 (9 pgs).
Ryan et al., "Fabrication methods of porous metals for use in orthopaedic applications," Biomaterials 27, 2006, pp. 2651-2670 (20 pgs).
Wang et al., "Biomimetic Modification of Porous TiNbZr Alloy Scaffold for Bone Tissue Engineering," Tissue Engineering: Part A, vol. 00, No. 00, 2009, pp. 1-8, (8 pgs).
Wang, M., "Composite Scaffolds for Bone Tissue Engineering," American Journal of Biochemistry and Biotechnology 2 (2), 2006, pp. 80-83 (4 pgs).
U.S. Appl. No. 12/961,209, filed Dec. 6, 2010.
U.S. Appl. No. 13/713,885, filed Dec. 13, 2012.
U.S. Appl. No. 14/030,840, filed Sep. 18, 2013.
U.S. Appl. No. 14/174,628, filed Feb. 6, 2014.
U.S. Appl. No. 14/328,567, filed Jul. 10, 2014.
U.S. Appl. No. 14/494,940, filed Sep. 24, 2014.
U.S. Appl. No. 14/517,312, filed Oct. 17, 2014.
U.S. Appl. No. 14/696,130, filed Apr. 24, 2015.
U.S. Appl. No. 14/707,944, filed May 8, 2015.
U.S. Appl. No. 14/696,130, filed Apr. 24, 2015, Wong.
U.S. Appl. No. 14/707,944, filed May 8, 2015, Wong.
Office Action issued in U.S. Appl. No. 14/696,130, dated Nov. 3, 2015 (24 pgs).

(56) References Cited

OTHER PUBLICATIONS

Office Action issued in U.S. Appl. No. 14/707,944, dated Jan. 29, 2016 (13 pgs).

Office Action issued in U.S. Appl. No. 14/871,677, dated May 13, 2016 (15 pgs).

International Preliminary Report on Patentability, issued in application No. PCT/US2014/061385, dated May 12, 2016 (8 pgs).

* cited by examiner

BIOCOMPATIBLE EXTREMELY FINE TANTALUM FILAMENT SCAFFOLDING FOR BONE AND SOFT TISSUE PROSTHESIS

CROSS REFERENCE TO RELATED APPLICATION

This Application is a continuation-in-part (CIP) of my U.S. application Ser. No. 14/328,567, filed Jul. 10, 2014, now U.S. Pat. No. 9,155,605, the contents of which are incorporated herein by reference.

FIELD OF THE INVENTION

The present invention relates to improvements in filament materials. The invention has particular utility in connection with biocompatible filament materials for use as scaffolding agents for repair and regeneration of defective bone tissue and as a porous metal coating of solid body parts as replacement such as for knee, hip joints as well as for soft tissue fibers such as nerve, tendons, ligaments, cartilage, and body organ parts, and will be described in connection with such utility, although other utilities such as for use in electrochemical cells, i.e. batteries, are contemplated.

BACKGROUND ART

There is a substantial body of art describing various materials and techniques for using biocompatible implants in the human body. Some of the more important needs are for hip joints, knee and spine reconstruction and shoulder joints. These implants are usually metallic since they are load bearing structures and require relatively high strengths. To insure proper fixation to the bone, a porous metal coating is applied to the implant surface, and is positioned such that it is in contact to the bone. This is to promote bone growth into and through the porous coating to insure a strong bond between the bone and the metallic implant. This coating requires a high degree of porosity, typically greater than 50% and as high as 70-80% with open connective pore sizes varying from $100\mu$ to $500\mu$. These implants must have significant compression strength to resist loads that these joints can experience. The modulus must also be closely matched to that of the bone to avoid stress degradation of the adjoining tissue.

In addition to the use of tantalum fibers for bone growth, repair and attachment of the implant, it can also be used effectively as a scaffold for soft tissue growth and can provide either a permanent or temporary support to the damage tissue/organ until functionalities are restored. Regardless of whether it's soft or hard tissue repair/replacement, all biomaterial will exhibit specific interactions with cells that will lead to stereotyped responses. The ideal choice for any particular material and morphology will depend on various factors, such are osteoinduction, Osteoconduction, angiogenesis, growth rates of cells and degradation rate of the material in case of temporary scaffolds.

Tissue engineering is a multidisciplinary subject combining the principles of engineering, biology and chemistry to restore the functionality of damaged tissue/organ through repair or regeneration. The material used in tissue engineering or as a tissue scaffold can either be naturally derived or synthetic. Further classification can be made based on the nature of application such as permanent or temporary. A temporary structure is expected to provide the necessary support and assist in cell/tissue growth until the tissue/cell regains original shape and strength. These types of scaffolds are useful especially in case of young patients where the growth rate of tissues are higher and the use of an artificial organ to store functionality is not desired. However, in the case of older patients, temporary scaffolds fail to meet the requirements in most cases. These include poor mechanical strength, mismatch between the growth rate of tissues and the degradation rate of said scaffold. Thus older patients need to have a stronger scaffold, which can either be permanent or have a very low degradation rate. Most of the work on scaffolding has been done on temporary scaffolds owing to the immediate advantages realized of the materials used and the ease of processing. Despite early success, tissue engineers have faced challenges in repairing/replacing tissues that serve predominantly biomechanical roles in the body. In fact, the properties of these tissues are critical to their proper function in vivo. In order for tissue engineers to effectively replace these load-bearing structures, they must address a number of significant questions on the interactions of engineered constructs with mechanical forces both in vivo and in vitro.

Once implanted in the body, engineered constructs of cells and matrices will be subjected to a complex biomechanical environment, consisting of time-varying changes in stresses, strains, fluid pressure, fluid flow and cellular deformation behavior. It is now well accepted that these various physical factors have the capability to influence the biological activity of normal tissues and therefore may plays an important role in the success or failure of engineered grafts. In this regard, it is important to characterize the diverse array of physical signals that engineered cells experience in vivo as well as their biological response to such potential stimuli. This information may provide an insight into the long-term capabilities of engineered constructs to maintain the proper cellular phenotype.

Significant advances have been made over the last four decades in the use of artificial bone implants. Various materials ranging from metallic, ceramic and polymeric materials have been used in artificial implants especially in the field of orthopedics. Stainless steel (surgical grade) was widely used in orthopedics and dentistry applications owing to its corrosion resistance. However later developments included the use of Co—Cr and Ti alloys owing to biocompatibilities issues and bioinertness. Currently Ti alloys and Co—Cr alloys are the most widely used in joint prostheses and other biomedical applications such as dentistry and cardio-vascular applications. Despite the advantages of materials such as Ti and Co—Cr and their alloys in terms of biocompatibility and bio inertness, reports indicated failure due to wear and wear assisted corrosion. Ceramics was a good alternative to metallic implants but they too had their limitation in their usage. One of the biggest disadvantages of using metals and ceramics in implants was the difference in modulus compared to the natural bone. (The modulus of articular cartilage varies from 0.001-0.1 GPa while that of hard bone varies from 7-30 GPa). Typical modulus values of most of the ceramic and metallic implants used lies above 70 GPa. This results in stress shielding effect on bones and tissues which otherwise is useful in keeping the tissue/bone functional. Moreover rejection by the host tissue especially when toxic ions in the alloy, such as Vanadium in Ti alloy, are eluted causes discomfort in patients necessitating revisional operations to be performed. Polymers have modulus within the range of 0.001-0.1 GPa and have been used in medicine for applications which range from artificial implants, i.e., acetabular cup, to drug delivery systems owing to the advantages of being chemically inert, biodegradability and possessing properties, which lies close to the cartilage properties. With the developments in the use of artificial implants there were growing concerns on the biocompatibility of the materials used for artificial implants and the immuno-rejection by the host cells. This led to the research on the repair and regeneration of damaged organs and tissues, which started in 1980 with use of autologuous (use of grafts from same species) skin grafts. Thereafter the field of tissue engineering has seen rapid developments from the use of synthetic materials to naturally derived material that includes use of autografts, allografts and xenografts for repair or regeneration of tissues.

Surface area and surface terrain or topography is one of the important factors governing cell adhesion and proliferation, and there have been many studies carried out in recent times to investigate the suitability of materials such as spider webs and cover slips, fish scales, plasma clots, and glass fibers. Silk fibers also have been used extensively in surgical applications such as for sutures and artificial blood vessels. Cell adhesion to materials is mediated by cell-surface receptors, interacting with cell adhesion proteins bound to the material surface. In aiming to promote receptor medicated cell adhesion the surface should mimic the extracellular matrix (ECM). ECM proteins, which are known to have the capacity to regulate such cell behaviors as adhesion, spreading, growth, and migration, have been studied extensively to enhance cell-material interactions for both in vivo and in vitro applications. However, the effects observed for a given protein have been found to vary substantially depending on the nature of the underlying substrate and the method of immobilization. In biomaterial research there is a strong interest in new materials especially for metals, which combine the required mechanical properties with improved biocompatibility for bone implants and soft tissue repair and replacement.

The foregoing discussion of the prior art derives in large part from an article by Yarlagadda, et al. entitled Recent Advances and Current Developments in Tissue Scaffolding, published in Bio-Medical Materials and Engineering 15(3), pp. 159-177 (2005).

As noted supra, high surface area and surface terrain or topography is one of the important factors governing cell adhesion and proliferation. The greater the relative surface area, i.e., the greater the specific surface of the material the greater cell adhesion and proliferation. Prior attempts to increase specific surface area of materials used for implants generally involve making the material used for forming the implant as small as possible. However, making the material as small as possible adds significantly to material manufacturing cost, and also complicates handling.

See U.S. Pat. No. 5,030,233 to Ducheyne, who discloses a mesh sheet material for surgical implant formed of metal fibers having a fiber length of about 2 mm to 50 mm, and having a fiber diameter of about 20 to about 200 um. According to the '233 patent if the fiber length is more than about 50 mm, manufacturing becomes difficult. In particular, for fiber lengths in excess of about 50 mm, sieving the fibers becomes impractical if not impossible. If the diameter of the fibers is less than about 20 microns, it is difficult to maintain the average pore size of at least 150 µm needed to assure ingrowth of bony tissue. If the fiber diameter is greater than about 200 µm, the flexibility and deformability become insufficient.

See also U.S. Pat. No. 4,983,184 to Steinemann which describes the use of metallic fibers, circular in cross-section, and having a thickness of 5 to 20 micrometers, formed of titanium alloy, bundled together as 200 to 1000, or even up to 3000 fibers, for forming an alloplastic reinforcing material for soft tissue. More particularly, Steinemann teaches titanium and titanium alloys for producing artificial soft tissue components and/or for reinforcing natural soft tissue components comprising elongate titanium or titanium alloy wires of diameter 5 to 20 micron diameter, bundled together for use as an artificial soft tissue component and reinforcement for a soft tissue component in a human or animal. Pure tantalum metal is known to have excellent bio-compatible properties and has for many years been used in the medical field. Indeed, a paper by Bobyn, Stackpool, Hacking, Tanzer and Krygier in the Journal of Bone & Joint Surgery (Br), Vol. 81-B, No. 5, September, 1999, and in U.S. Pat. No. 5,282,861 to Kaplan describes the use of porous tantalum bio material for use to promote bone growth and adhesion of the metallic implants, which material currently is marketed by the Zimmer Corp.

SUMMARY OF THE INVENTION

It is well known that as the diameter of metal filaments are reduced below 25 microns, it becomes increasingly difficult to assemble these micron sized fiber into a scaffolding structure. The most important requirement is the need for the scaffold to maintain a sufficient solid and stable porosity structure during and after implantation into the body. The present invention provides this characteristic and retains the high specific surface area and improved mechanical performance. In particular, the invention provides elongate elements having cross-sectional shapes including elongate paths open on one side. By way of example, as can be seen in FIG. 1 and FIG. 2, a filament may consist of hollow sections having a Z-shape or flagged-Y-shape, inside a round filament constructed with tantalum or other biocompatible valve metal connectors which are thin, uniform in thickness and continuous in nature. However, other shapes are possible as will be described below. To insure lateral stability, the filaments can also be twisted to further the resistance to compressive forces. In addition, other geometric arrangement also can be made in similar fashion.

It is expected that depending on the specific requirement of the implant, the filament diameter can range from about 25 microns to about 250 microns, preferably about 50 microns, with the connector thickness between about 5 to about 50 microns.

In one aspect of the invention there is provided a tissue implant member for implanting in living tissue, comprising a mechanically stable flexible filament consisting essentially of thin open structural valve metal elements of uniform thickness which have a cross-sectional size of less than 250 microns.

Preferably, the valve metal is a metal selected from the group consisting of tantalum, titanium, niobium, hafnium and zirconium and their alloys.

In one embodiment the implant comprises a tissue scaffold for supporting tissue growth, preferably selected from the group consisting of bone, nerve cells, tendons, ligaments, cartilage and body organ parts.

The invention also provides a method for promoting tissue growth in a body comprising implanting in the body a tissue implant member as above described.

In one embodiment the tissue is selected from the group consisting of bone, nerve cells, tendon, ligaments or cartilage and body organ parts.

The invention also provides a tissue implant member for implanting in living tissue consisting essentially of a mechanically stable flexible structure of open structured tantalum elements in which the tantalum filaments have a cross-sectional size of less than 250 microns.

Preferably, the structural tantalum elements inside the filament have a cross-sectional thickness of from about 5 to less than about 50 microns, more preferably from about 2 to less than about 30 microns.

In one embodiment the implant comprises a tissue scaffold for supporting tissue growth.

Preferably, the tissue is selected from the group consisting of bone, nerve cells, tendon, ligaments, cartilage and body organ parts.

The present invention also provides a method for promoting tissue growth in a body comprising implanting in the body a tissue implant member as above described.

Preferably, the tissue is selected from the group consisting of bone, nerve cells, tendon, ligaments, cartilage and body organ parts.

BRIEF DESCRIPTION OF THE DRAWINGS

Further features and advantages of the present invention will be seen from the following detailed description taken in conjunction with the accompanying drawings, wherein.

DETAILED DESCRIPTION

As used herein, the term biocompatible valve metal includes tantalum, which is the preferred metal, as well as titanium, niobium, hafnium and zirconium and their alloys. The term "formed essentially of tantalum or other biocompatible valve metal" or "consisting essentially of tantalum or other biocompatible valve metal" means that the filaments comprise at least 99.0 percent by wt. tantalum or other biocompatible valve metal.

"Open structure" means shaped filaments having a cross-sectional shape including integral connectors.

Referring to FIGS. 1-5, the process starts with the fabrication of valve metal filaments, such as tantalum, by combining shaped elements 8 of tantalum (see FIGS. 1 and 2) with a ductile material, such as copper to form a billet at step 10. The shaped elements of tantalum are formed from thin sheets of tantalum typically between 0.25 mm to 0.50 mm thick. The elements are structured such that they preform as a round filament. Between the tantalum elements, copper is placed and is removed after the billet is extruded and drawn to the desired final size following the teachings of my prior PCT application nos. PCT/US07/79249 and PCT/US97/23260, and U.S. Pat. Nos. 7,146,709 and 7,480,978.

The billet is then sealed in an extrusion can in step 12, and extruded and drawn in step 14 following the teachings of my prior PCT applications Nos. PCT/US07/79249 and PCT/US08/86460, or my prior U.S. Pat. Nos. 7,480,978 and 7,146,709. In one example, the extruded and drawn filaments are cut or chopped into short segments, typically 0.15875 to 0.63500 cm inch long at a chopping station 16.

Preferably the cut filaments all have approximately the same length. Actually, the more uniform the filaments in size, the better. The chopped filaments are then passed to an etching station 18 where the ductile metal is leached away using a suitable acid. For example, where copper is the ductile metal, the etchant may comprise nitric acid.

Figure 1:
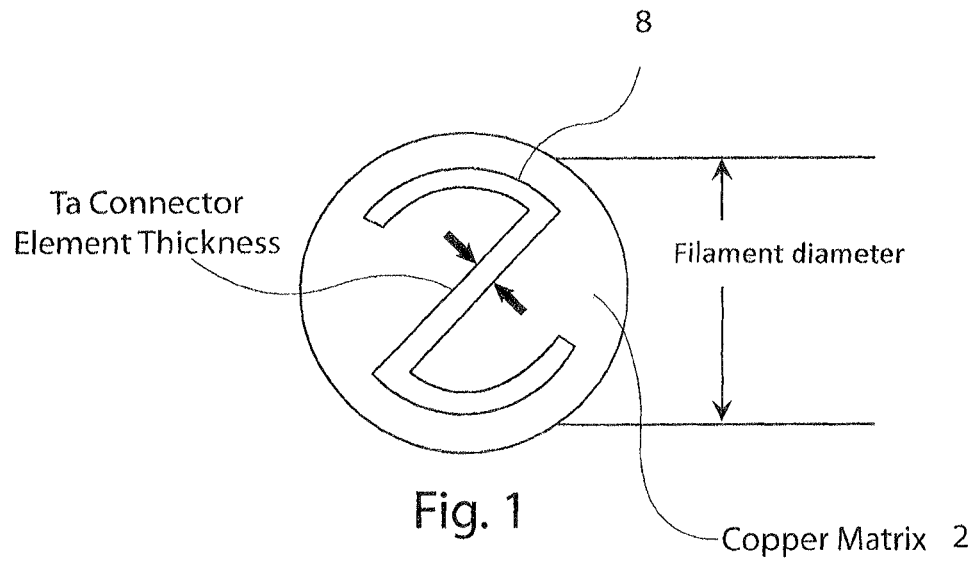
FIGS. 1 and 2 illustrate starting members in accordance with the present invention.
Figure 2:
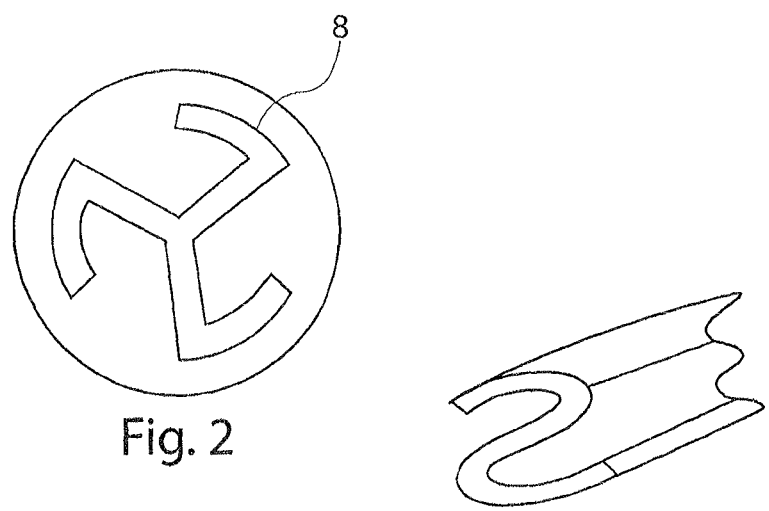
Figure 4:
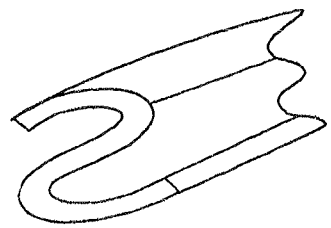
FIG. 4 is a member formed in accordance with the present invention.
Figure 3:
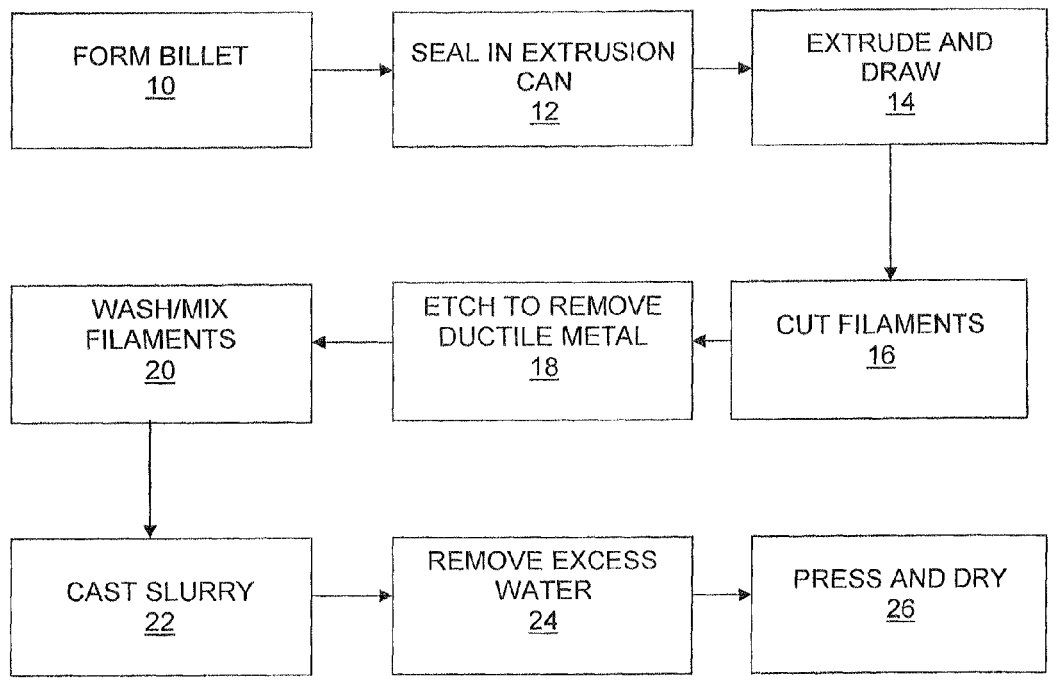
FIG. 3 is a schematic block diagram of a process for forming implant tissue members in accordance with the present invention.
Figure 5:
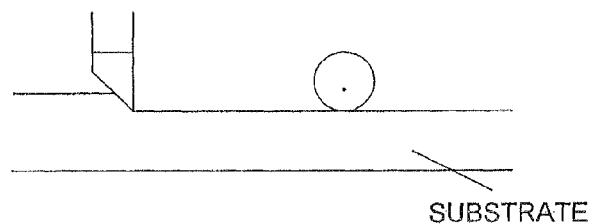
FIG. 5 is a simplified side elevational view showing casting of a member in accordance with the present invention.

Etching in acid removes the copper from between the tantalum filaments. After etching, one is left with a plurality of short filaments of tantalum 15, as shown in FIG. 4. The tantalum filaments are then washed in water, and the wash water is partially decanted to leave a slurry of tantalum filaments in water. The slurry of tantalum filaments in water is uniformly mixed and is then cast as a thin sheet using, for example, in FIG. 5 "Doctor Blade" casting station 22. Excess water is removed, for example, by rolling at a rolling station 24. The resulting mat is then further compressed and dried at a drying station 26.

It was found that an aqueous slurry of chopped filaments will adhere together and was mechanically stable such that the fibers easily could be cast into a fibrous sheet, pressed and dried into a stable mat.

The resulting fibrous structure is flexible and has sufficient integrity so that it can be assembled and shaped into an elongate scaffolding where it can then be used. The fibrous structure product made according to the present invention forms a porous surface of fibers capable of maintaining minimum spacings between fibers with large surface area-to-volume, which encourages healthy ingrowth of bone or soft tissue.

Figure 6A:
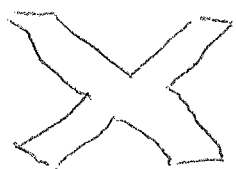
FIGS. 6A-6D illustrates cross-sectional views of other members in accordance with the present invention.
Figure 6B:
Figure 6C:
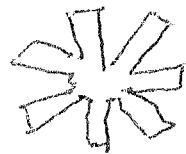
Figure 6D:

Various changes may be made in the above without departing from the spirit and scope thereof. More particularly, other shaped fibers having elongate open pads may be formed. By way of example, as shown in FIG. 6A, the fibers may have a X-shape, in cross-section, or a W-shape in cross-section as illustrated in FIG. 6B, a starburst shape as shown in FIG. 6C, a U-shape as shown in FIG. 6D, which I have given as exemplary. The point is the elongate elements may have a variety of cross-sectional shapes that form structurally elongate paths open on one side.

The resulting fibrous structure made in accordance with the present invention has significant advantages over prior art structures formed from solid round filaments. The open structure of the filaments adds significantly to filament surface area which, as noted supra, adds advantages in terms of cell adhesion and proliferation. Moreover, these filaments can maintain a parallel path—rigid in one direction, to allow tissue to grow on a flat plane driven surface. Conventional small diameter solid round filaments adhere in tight bundles, especially when wet, essentially parallel to one another due to surface tension forces, and causes problems in maintaining an open porosity. By changing filament structural geometry, we can avoid this problem and maintain separation of each and every filament and still provide high specific surface area.

Numerous other arrangements by carding the fibers, meshes, braids and other type arrangements can also be constructed.

Moreover, while the invention has been described in particular for use in connection with biocompatible filament materials for use as scaffolding agents for repair and regeneration of body parts such as bone tissue, nerve, tendons, etc., the elongate filaments having elongate pads open on one side also advantageously may be used in applications where high surface area filaments are desired such as, for example, for use in forming anodes for electrochemical cells, i.e. batteries and/or semi-solid electrodes for use in high density electrochemical cells such as lithium batteries.

The invention claimed is:

1. A tissue implant member for implanting in living tissue, comprising a mechanically stable structure consisting essentially of thin, elongate elements, each having a long axis, formed of a valve metal, each of said elements having at least one structurally fixed channel forming an elongate pathway extending from a surface of said element parallel to the element long axis, said at least one channel being open on at least one side, each of said elements having a cross-sectional size of less than 250 microns.

2. The implant as claimed in claim 1, wherein said valve metal elements have a cross-sectional size of less than about 50 microns.

3. The implant as claimed in claim 1, wherein the valve metal is a metal selected from the group consisting of tantalum, titanium, niobium, hafnium and zirconium and their alloys.

4. The implant of claim 1, wherein the implant comprises a tissue scaffold for supporting tissue growth.

5. A method for promoting tissue growth in a body comprising implanting in the body a tissue implant member as claimed in claim 1.

6. The method of claim 5 wherein the tissue is selected from the group consisting of bone, nerve cells, tendon, ligaments or cartilage and body organ parts.

7. A tissue implant member for implanting in living tissue consisting essentially of thin, elongate open shape elements, each having a long axis, formed of tantalum, each of said elements having at least one structurally fixed channel forming an elongate pathway extending from a surface of said element parallel to the element long axis, said at least one channel being open on one side, each of said elements having a cross-sectional size of less than 250 microns.

8. The implant as in claim 7, wherein said structural tantalum elements have a cross-sectional size of from about 5 to less than about 50 microns.

9. The implant of claim 8, wherein the implant comprises a tissue scaffold for supporting tissue growth.

10. The implant as in claim 7, wherein said structural tantalum elements have a cross-sectional size of from about 2 to less than about 50 microns.

11. The implant as in claim 10, wherein the implant comprises a tissue scaffold for supporting tissue growth.

12. A method for promoting tissue growth in a body comprising implanting in the body a tissue implant member as claimed in claim 7.

13. The method of claim 12, wherein the tissue is selected from the group consisting of bone, nerve cells, tendon, ligaments, cartilage and body organ parts.

14. An elongate filament comprising a mechanically stable structure consisting essentially of thin, elongate elements, each having a long axis, formed of a valve metal, each of said elements having at least one structurally fixed channel forming an elongate pathway extending from a surface of said element parallel to the element long axis, said at least one channel being open on one side, each of said elements having a cross-sectional size of less than 250 microns.

15. The filament as claimed in claim 14, wherein said valve metal elements have a cross-sectional size of less than about 50 microns.

16. The filament as claimed in claim 14, wherein the valve metal is a metal selected from the group consisting of tantalum, titanium, niobium, hafnium and zirconium and their alloys.

* * * * *